United States Patent
Konofal et al.

(10) Patent No.: US 10,456,387 B2
(45) Date of Patent: Oct. 29, 2019

(54) PHACETOPERANE FOR TREATING OF ATTENTION DEFICIT HYPERACTIVITY DISORDER

(71) Applicant: NLS PHARMA AG, Stans (CH)

(72) Inventors: Eric Konofal, Senlis (FR); Bruno Figadere, Saint Cheron (FR)

(73) Assignee: NLS PHARMACEUTICS AG, Stans (CH)

( * ) Notice: Subject to any disclaimer, the term of this patent is extended or adjusted under 35 U.S.C. 154(b) by 0 days.

(21) Appl. No.: 15/913,481

(22) Filed: Mar. 6, 2018

(65) Prior Publication Data

US 2018/0214436 A1 Aug. 2, 2018

Related U.S. Application Data

(63) Continuation of application No. 14/360,355, filed as application No. PCT/FR2012/052749 on Nov. 29, 2012, now abandoned.

(30) Foreign Application Priority Data

Nov. 29, 2011 (FR) ...................... 11 60902

(51) Int. Cl.
*A61K 31/4458* (2006.01)
*C07D 211/22* (2006.01)
*A61K 31/445* (2006.01)

(52) U.S. Cl.
CPC ........ *A61K 31/4458* (2013.01); *A61K 31/445* (2013.01); *C07D 211/22* (2013.01); *Y02P 20/55* (2015.11)

(58) Field of Classification Search
CPC . A61K 31/445; A61K 31/4458; C07D 211/22
See application file for complete search history.

(56) References Cited

U.S. PATENT DOCUMENTS 2,928,835 A 3/1960 Jacob et al.
6,344,215 B1 2/2002 Bettman et al.

OTHER PUBLICATIONS

Dobkin, Anesthesia, vol. 15, No. 2, Apr. 1960 (Year: 1960).*
Nair et al., "A simple practice guide for dose conversion between animals and human," Department of Pharmaceutical Sciences, College of Clinical Pharmacy, King Faisal University, Saudi Arabia, © 2016 Journal of Basic and Clinical Pharmacy, www.jbclinpharm.org.
2-Piperidinemethanol, www.alphachimica.com.
Bizot et al., Effects of atomoxetine, desipramine, D-amphetamine and methylphenidate on impulsivity in juvenile rats, measured in a T-maze procedure, Neuroscience Letters, www.elsevier.com/locate/neulet, pp. 20-24.
Budman et al., "Tourette's Syndrome", Current Clinical Neurology: Psychiatry for Neurologists, Text revision Diagnostic and Statistical Manual of Psychiatry, Fourth Edition (DSM-IV-TR).
Drouin et al., "aX1b-Adrenergic Receptors Control Locomotor and Rewarding Effects of Psychostimulants and Opiates", The Journal of Neuroscience, Apr. 1, 2002, 22(7): 2873-2884.
Bizot et al., Examination of potential addictive effects of phacetoperane, a new compound in development for ADHD, NLS.
Premiers resultats cliniques de l'emploi d'un nouveau, psychotonique, le 8228 R.P., par MM. SIVADON, Chanoit AzouLAY, Societe Medico-Psychologique, pp. 537-541.
Opiophile, http://forum.opiophile.org/showthread.php?25721-Stimulants-that-would-make-goodmeds&s=dd38ea19d8268cf2c55cec25dc46a1 07, publicly available on Aug. 24, 2009.
Bluelight, http://www.bluelight.org/vb/threads/362377-Ethyi-Ester-Analogues-of-DARis, publicly available on Oct. 2, 20008.
Rosier et al, World J Bioi. Psychiatry. Aug. 2010; 11 (5):709-18.
Wen et al, Oral Controlled Release Formulation Design and Drug Delivery, Copyrighted(@) 2010.
Leitch, et al., "A trial of pour anti-depressant drugs", Psychopharmacolxxiia, vo. 4, No. 1, 1963 Examiner.
Exhibit C: Jul. 13, 1959, Conference Report, Société Médico-Psychologique, now with an English translation.
S. Melendez, "In a World of Opiate Addicts, the Internet Plays Doctor and Therapist," Motherboard Blog, published Jan. 15, 2014, accessed Jan. 10, 2019 at https://motherboard.vice.com/en_us/article/d738dv/in-a-world-of-opiate-addicts-the-internet-plays-doctor-and-therapist.
Methylphenidate-based Novel Psychoactive Substances: A review of the evidence of use and harm, Advisory Council on the Misuse of Drugs, United Kingdom, Mar. 31, 2015.
Methylphenidate-based Novel Psychoactive Substances: A review of the evidence of use and harm, Advisory Council on the Misuse of Drugs, United Kingdom, Mar. 10, 2017.
Horn et al., "Dopamine Uptake: A Review of Progress in the Last Decade," Progress in Neurobiology, 34 (1990), pp. 387-400. Exhibit L.
Walter, "Monoamine Reuptake Inhibitors: Highlights of Recent Research Developments," Drug Development Research, 65 (2005), pp. 97-118.

* cited by examiner

*Primary Examiner* — Jean P Cornet
(74) *Attorney, Agent, or Firm* — Finnegan, Henderson, Farabow, Garrett & Dunner LLP

(57) ABSTRACT

The invention relates to the treatment of an attention deficit hyperactivity disorder (ADHD) with alpha-phenyl(piperidin-2-yl)methanol, or the pharmaceutically acceptable salts and esters thereof, in particular the acetate derivative, more particularly dextrophacetoperane. The invention additionally provides a method of synthesis of the (S,S) enantiomer of alpha-phenyl(piperidin-2-yl)methanol as well as a method of synthesis of dextrophacetoperane.

9 Claims, 1 Drawing Sheet

PHACETOPERANE FOR TREATING OF ATTENTION DEFICIT HYPERACTIVITY DISORDER

CROSS-REFERENCE TO RELATED APPLICATION

This application is a continuation of U.S. application Ser. No. 15/360,355, filed on Oct. 14, 2014, which is a national phase of International Application No. PCT/FR2012/052749, filed on Nov. 29, 2012, which claims the benefit of French Application No. 1160902, filed on Nov. 29, 2011. The contents of the above-referenced applications are expressly incorporated herein by reference in their entireties.

The invention relates to the treatment of attention deficit hyperactivity disorder.

TECHNOLOGICAL BACKGROUND OF THE INVENTION

Attention deficit hyperactivity disorder (ADHD) is a combination of behavioural hyperactivity, inattentiveness, and impulsiveness. Diagnosis is based on clinical criteria defined in the Diagnostic and Statistical Manual of Mental Disorders (DSM-IV TR). ADHD is first and foremost the exaggerated, permanent and continual expression of behavioural manifestations that are not due to educational, pedagogical or socio-economic deprivation.

This disorder is a frequent reason for consultation in child psychopathology. According to studies, its prevalence in the general child population is from 2 to 5%. The signs of inattentiveness may persist beyond childhood and are responsible for social, relational and affective difficulties. Up to 60% of children with ADHD continue to present characteristic symptoms at adult age, although the typical presentation corresponds to completely different criteria (work, relationships, parenthood, etc.). Studies have shown that the disorder is clinically significant at adult age, with dysfunction in professional, familial and affective respects. Moreover, comorbidity is high, and can complicate diagnosis and treatment.

Ritalin® (methylphenidate hydrochloride) is currently the drug most prescribed for treating ADHD, but it is not free from side-effects, which can be severe.

There is still a need for an effective drug for treating ADHD, which should preferably be less toxic than Ritalin.

SUMMARY OF THE INVENTION

The invention relates to alpha-phenyl(piperidin-2-yl)methanol, or a pharmaceutically acceptable salt or ester thereof, for use in the treatment of ADHD.

Preferably the acetate of alpha-phenyl(piperidin-2-yl)methanol in the threo form (phacetoperane) is used, or a pharmaceutically acceptable salt thereof.

In a particular embodiment, said phacetoperane is in its dextrorotatory form.

In another particular embodiment, said phacetoperane is in its laevorotatory form.

In addition, the invention provides a method of synthesis of the (S,S) enantiomer of alpha-phenyl(piperidin-2-yl)methanol as well as a method of synthesis of dextrophacetoperane.

LEGEND OF THE FIGURES

Figure 1:
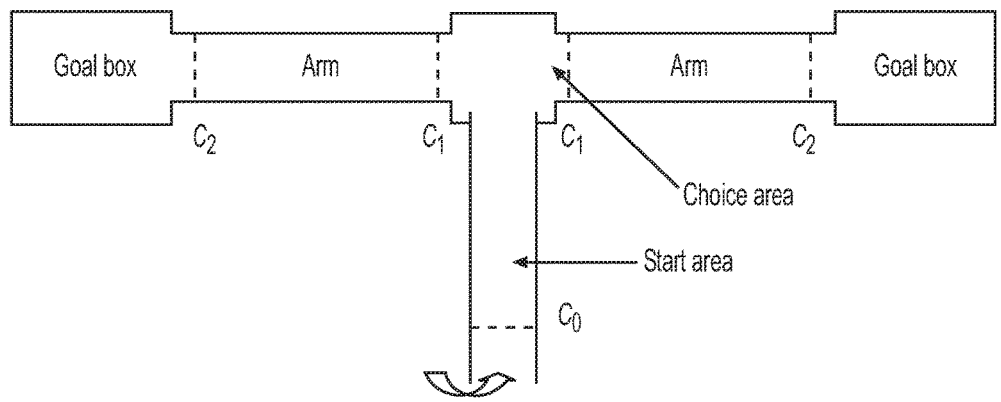

FIG. 1 is a schematic diagram of the T-maze test: c0, c1 and c2 are the limits of the guillotine doors.

Figure 2:
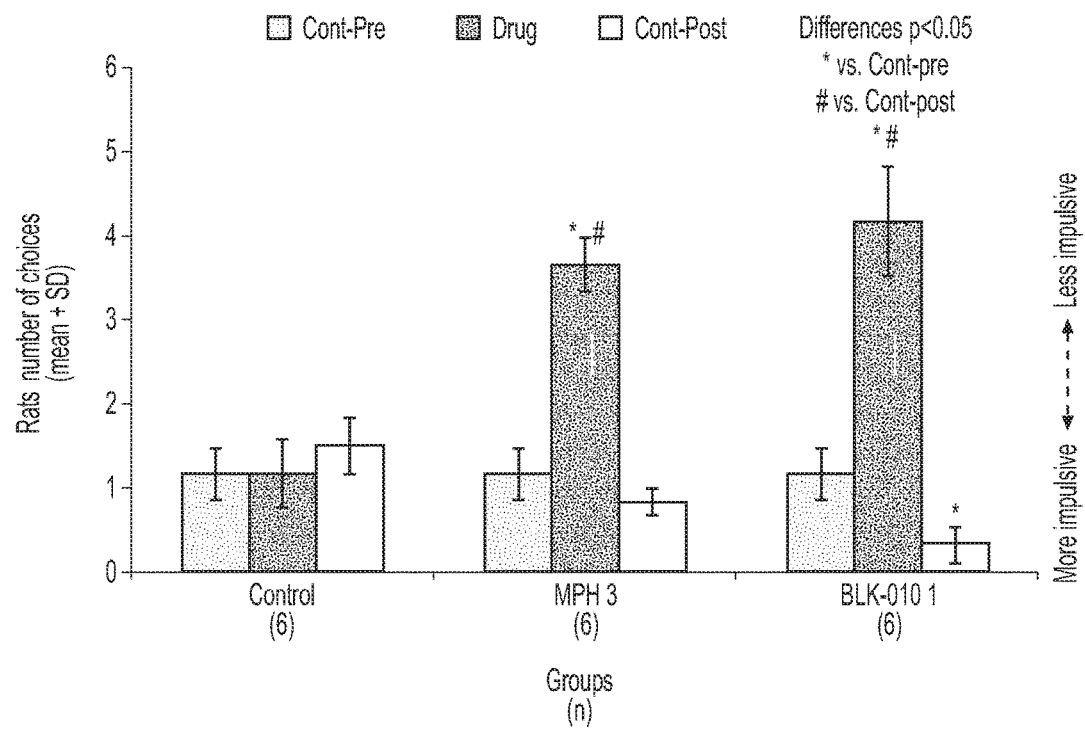

FIG. 2 presents a bar-chart comparison of a behavioural test on the juvenile rat, submitted to the T-maze test, a model of ADHD. It shows the results in the "pre-medication" phase (left columns), "medication" phase (middle columns), and "post-medication" phase (right columns). The number of times the rat chooses the reward that is large but is deferred by 30 s is an indicator of the level of impulsiveness (the higher the number of choices, the less the animal is regarded as impulsive). Phacetoperane is compared with methylphenidate.

DETAILED DESCRIPTION OF THE INVENTION

Definitions

According to the invention, the term "treatment" signifies therapeutic or prophylactic treatment of ADHD or of one of its symptoms, in particular lack of attention, hyperactivity, or impulsiveness. This term includes improvement of the symptoms of the disease.

The "patient" with ADHD is a human: child, adolescent or adult. More particularly, the patient is a subject of normal intelligence, evaluated by an Intelligence Quotient test above 80 (by an evaluation of intelligence, such as WISC-IV, for example). Therefore the subject does not present any mental impairment or delayed development, including behavioural or motor disorders connected with delayed mental development (backwardness), such as oligophrenia or hyperkinesia of neurological origin.

According to the invention, an "erythro diastereoisomer" of a compound having two asymmetric carbons includes the (R,S) enantiomer and the (S,R) enantiomer of said compound as well as the racemic mixtures thereof.

A "threo diastereoisomer" of a compound having two asymmetric carbons includes the (R,R) enantiomer and the (S,S) enantiomer of said compound as well as the racemic mixtures thereof.

In the context of the present invention, the compound of formula (A):

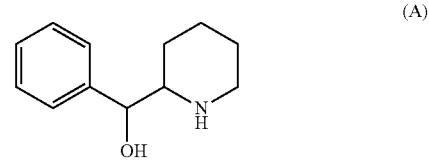 [SMILES: OC(c1ccccc1)C1CCCCN1]

(A)

is denoted indiscriminately as alpha-phenyl-2-piperidinemethanol or phenyl(piperidin-2-yl)methanol, or else alpha-phenyl(piperidin-2-yl)methanol.

"Phacetoperane" means the threo diastereoisomer of alpha-phenyl-2-piperidinemethanol acetate. Alpha-phenyl-2-piperidinemethanol acetate is also called hereinafter phenyl(piperidyn-2-yl)methyl acetate or alpha-phenyl(piperidyn-2-yl)methyl acetate and is represented by formula (B).

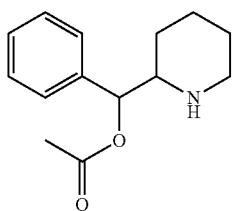

(B)

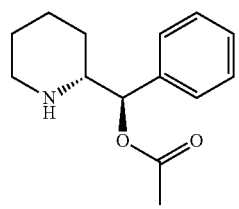

(I)

Hereinafter, levophacetoperane means the laevorotatory enantiomer of phacetoperane, i.e. the (R,R) enantiomer.

Similarly, dextrophacetoperane means the dextrorotatory enantiomer of phacetoperane, i.e. the (S,S) enantiomer.

Compounds for Use in the Invention:

The compounds for use in the invention are alpha-phenyl (piperidin-2-yl)methanol of formula (A), or the pharmaceutically acceptable salts and esters thereof, alone or mixed.

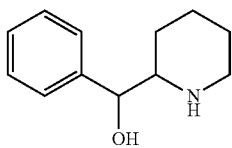

(A)

In particular the ester in the form of acetate is preferred.

Alpha-phenyl-2-piperidinemethanol acetate of formula (B) was synthesized in the 1950s under code 7890RP, by the Research Laboratories of the company Rhône Poulenc (cf. U.S. Pat. No. 2,928,835).

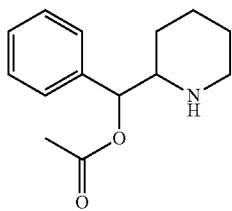

(B)

The present invention relates to the various threo and erythro diastereoisomers of alpha-phenyl(piperidin-2-yl) methanol, the pharmaceutically acceptable salts and esters thereof, whether in racemic form or in enantiomeric form.

Preferably, the present invention relates to the threo diastereoisomers of these compounds.

In a preferred embodiment, the present invention relates to the threo diastereoisomer of alpha-phenyl(piperidin-2-yl) methyl acetate, or a pharmaceutically acceptable salt thereof, for use in the treatment of an attention deficit hyperactivity disorder (ADHD). In a particular embodiment, the threo diastereoisomer of alpha-phenyl(piperidin-2-yl) methyl acetate, or a pharmaceutically acceptable salt thereof, is used in racemic form, i.e. in the form of a mixture of its (S,S) and (R,R) enantiomers.

In another embodiment, the laevorotatory form of alpha-phenyl(piperidin-2-yl)methyl threo-acetate or a pharmaceutically acceptable salt thereof is used. The laevorotatory form corresponds to the (R,R) enantiomer. This form, initially coded 8228RP, was then denoted by levophacetoperane (formula I).

In an additional embodiment, the dextrorotatory form of alpha-phenyl(piperidin-2-yl)methyl threo-acetate is used, i.e. the (S,S) enantiomer, which can be designated here as dextrophacetoperane of formula (II).

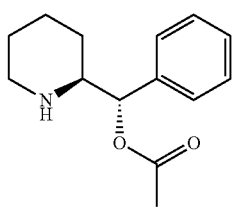

(II)

Without wishing to be bound to any theory, the applicant is of the opinion that the use of the dextrorotatory enantiomer of phacetoperane or of a racemic mixture enriched in the dextrorotatory enantiomer of phacetoperane is advantageous when we wish to treat ADHD without causing a sedative effect in the patient.

"A racemic mixture of phacetoperane enriched in the dextrorotatory enantiomer" means a mixture for which the molar percentage of dextrorotatory enantiomer (i.e. (S,S)) is above 50%, preferably above 70% and even more preferably above 90%, the molar percentage of dextrorotatory enantiomer being calculated relative to the total number of moles of phacetoperane in said mixture.

A molar percentage of dextrorotatory enantiomer above 90% includes a percentage of dextrorotatory enantiomer above 92%, above 93%, above 94%, above 95%, above 96%, above 97%, above 98%.

Preferably, dextrophacetoperane is used in the context of the invention, more preferably in the form of a salt, for example a hydrochloride.

Method of Synthesis of the Compounds of the Invention:

The compounds of the invention can be produced by any method known by a person skilled in the art. A person skilled in the art will be able in particular to refer to U.S. Pat. No. 2,928,835, which describes the production of phacetoperane in racemic form and in laevorotatory form.

In general, phacetoperane, or a salt thereof, in racemic form or in the form of (S,S) or (R,R) enantiomer, can be obtained from alpha-phenyl-(piperidin-2-yl)-methanol in the threo form.

Threo-alpha-phenyl-(piperidin-2-yl)-methanol can be obtained according to the following reaction scheme:

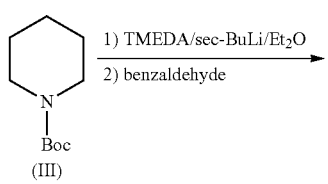

(III)

-continued

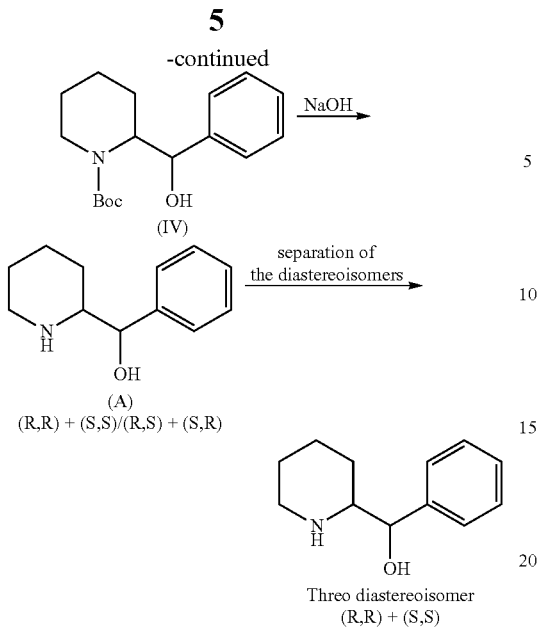

This reaction scheme comprises the following steps:
1. alpha-lithiation of the N-Boc piperidine derivative (III) followed by electrophilic substitution of the intermediate formed in the presence of benzaldehyde so as to obtain the N-(Boc)-α-phenyl(piperidin-2-yl)methanol derivative (IV). It goes without saying that the Boc group can be replaced with any other protecting group known by a person skilled in the art for protecting the amine function,
2. treatment of the N-(Boc)-α-phenyl(piperidin-2-yl) methanol derivative (IV) in a basic medium to obtain phenyl(piperidin-2-yl)methanol in the form of a diastereoisomeric mixture, and
3. separation of the threo diastereoisomer of alpha-phenyl-(piperidin-2-yl)-methanol from the erythro diastereoisomer, which can be carried out by any suitable method of separation. It can be, for example, a step of silica column chromatography of the mixture of diastereoisomers obtained in step 2 using a suitable eluent.

Phacetoperane in racemic form can be obtained by acetylation of the diastereoisomer of alpha-phenyl-(piperidin-2-yl)-methanol obtained in step 3.

Phacetoperane in the form of (R,R) or (S,S) enantiomer can be obtained:
by splitting the phacetoperane in racemic form or
by splitting the threo-phenyl-(piperidin-2-yl)-methanol in racemic form followed by acetylation of the enantiomer or enantiomers isolated.

Splitting of phacetoperane or threo-phenyl-(piperidin-2-yl)-methanol can be carried out by conventional methods of enantiomeric resolution, for example by chiral stationary phase chromatography or by preferential crystallization using a splitting agent, generally a chiral compound such as tartaric acid, camphorsulphonic acid, dibenzoyltartaric acid or else N-acetyl leucine.

As an example, U.S. Pat. No. 2,928,835 describes separation of the (S,S) and (R,R) enantiomers of threo-phenyl-(piperidin-2-yl)-methanol by fractional crystallization using (−)dibenzoyltartaric acid in propanol. In the specific conditions described in U.S. Pat. No. 2,928,835, the dextrorotatory enantiomer remains in solution whereas the laevorotatory enantiomer is precipitated in the form of dibenzoyltartrate salt. Similarly, it is expected that the use of (+)-dibenzoyltartanric acid would allow selective crystallization of the dextrorotatory enantiomer of phacetoperane.

The applicant has shown that reduction of the Boc derivative of phenyl-(piperidin-2-yl)-methanone by lithium tri-sec-butylborohydride (L-Selectride®) gives a key intermediate for obtaining dextrophacetoperane, namely alpha-phenyl-(piperidin-2-yl)-methanol in the form of (S,S) enantiomer, optionally in protected form.

Thus, an additional object according to the invention is a method of preparing the compound in the form of (S,S) enantiomer of formula (VI):

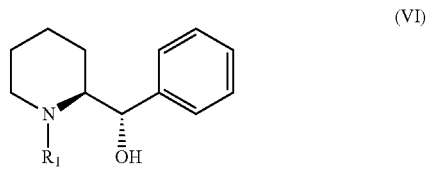

in which $R_1$ represents a hydrogen or a protecting group, said method comprising reduction of the compound of formula (V)

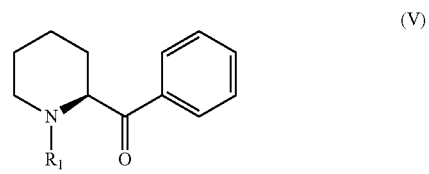

by an alkaline salt of tri-sec-butylborohydride.

The alkaline salts of tri-sec-butylborohydride include the lithium, potassium, and sodium salts.

In a preferred embodiment, the alkaline salt of tri-sec-butylborohydride is lithium tri-sec-butylborohydride.

The protecting group can be any protecting group of the amine function known by a person skilled in the art. In particular, it can be a group that generates steric hindrance. In particular it can be the Boc group (tert-butyloxycarbonyl).

In a particular embodiment of this method, $R_1$ is a Boc group and the alkaline salt of tri-sec-butylborohydride is lithium tri-sec-butylborohydride.

The compound of formula (V) corresponds to (S)-phenyl-(piperidin-2-yl)-methanone in protected or unprotected form. (S)-phenyl-(piperidin-2-yl)-methanone can be obtained by any method known by a person skilled in the art.

The applicant has shown that this compound can be obtained advantageously by reaction of a Weinreb amide with a suitable organometallic compound.

In a particular embodiment, the method according to the invention comprises the following steps:
(i) reaction of the compound of formula (VII)

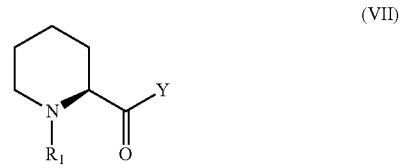

in which $R_1$ represents H or a protecting group and Y represents OH, F, Cl, Br or $OCH_3$, with an N,O-dialkylhydroxylamine of formula $NHR_2OR_2$ in which $R_2$ represents an alkyl, preferably $C_1$-$C_6$, to obtain the compound of formula (VIII)

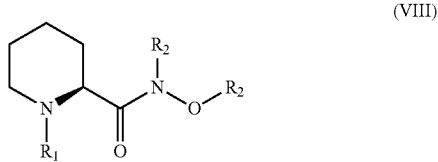

(VIII)

(ii) reaction of the compound of formula (VIII) with an organometallic compound PhM in which Ph represents a phenyl group and M represents Li, MgX or ZnX with X being a halide selected from I, Br and Cl to obtain the compound of formula (V)

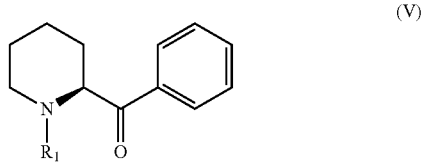

(V)

(iii) reduction of the compound of formula (V) by an alkaline salt of tri-sec-butylborohydride to obtain the alcohol of formula (VI) or a salt thereof, in the form of (S,S) enantiomer

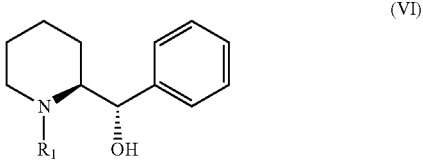

(VI)

In certain embodiments of the method according to the invention, step (i) of the method is characterized by one, several or all of the following characteristics:
Y is OH,
$R_2$ is Me, and
PhM is phenyl lithium In step (i), when the compound of formula (VII) is a carboxylic acid (Y=OH), the reaction between said carboxylic acid and the N,O-dialkylhydroxylamine can be carried out using one or more peptide coupling agents such as the carbodiimides and the phosphonium salts. We may mention as an example of peptide coupling agents, benzotriazol-1-yl-oxy-tris-(dimethylamino)-phosphonium hexafluorophosphate.

It goes without saying that each step of the method according to the invention can be carried out in the presence of a solvent and, optionally, in the presence of a base or an acid.

The method of preparing the compound of formula (VI) in the form of (S,S) enantiomer can be used advantageously in the preparation of alpha-phenyl(piperidin-2-yl)methanol acetate in the form of (S,S) enantiomer.

Thus, an additional object of the invention is a method of preparing the (S,S) enantiomer of alpha-phenyl(piperidin-2-yl)methanol acetate (dextrophacetoperane) or a pharmaceutically acceptable salt thereof, said method comprising the following steps
preparation of the compound of formula (VI) in the form of (S,S) enantiomer as disclosed above, and
acetylation of the compound of formula (VI), optionally followed by deprotection of the amine function of the piperidine group when $R_1$ is a protecting group.

In other words, the method of preparing the (S,S) enantiomer of alpha-phenyl(piperidin-2-yl)methyl acetate (dextrophacetoperane) or a pharmaceutically acceptable salt thereof according to the invention comprises the following steps:
reduction of the compound of formula (V) by an alkaline salt of tri-sec-butylborohydride

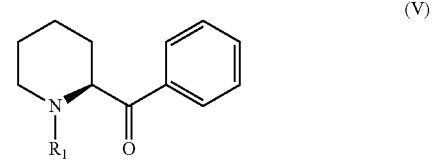

(V)

in which $R_1$ represents H or a protecting group, to obtain the alcohol or a salt thereof, in the form of (S,S) enantiomer of formula (VI):

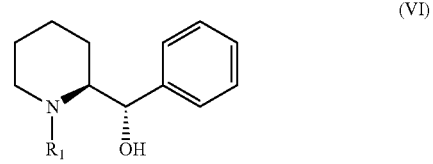

(VI)

acetylation of the alcohol of formula (VI), optionally followed by deprotection of the amine function of the piperidine group when $R_1$ is a protecting group.

The acetylation step can be carried out by methods well known by a person skilled in the art, in particular by reacting the alcohol of formula (VI) with acetic anhydride or ethanoyl chloride.

Regarding the protecting groups of the amine function as well as the methods for introduction or cleavage thereof, reference can be made to the reference work by Greene (Greene's Protective Groups in Organic Synthesis, 2006, John Wiley & Sons Inc; 4th edition). If $R_1$ is a Boc group, the step of deprotection of the piperidine group can be carried out by acid hydrolysis for example in the presence of hydrochloric acid or trifluoroacetic acid.

In a particular embodiment, the method according to the invention comprises the following steps:
(i) reaction of the compound of formula (VII)

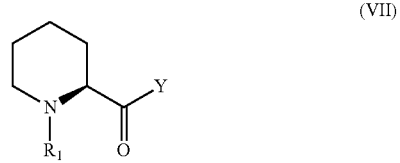

(VII)

in which $R_1$ represents H or a protecting group and Y represents OH, F, Cl, Br or $OCH_3$, with an N,O-dialkylhydroxylamine of formula $NHR_2OR_2$ in which $R_2$ represents an alkyl, preferably $C_1$-$C_6$, to obtain the compound of formula (VIII)

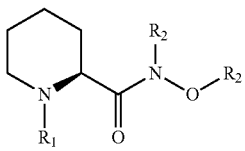

(VIII)

(ii) reaction of the compound of formula (VIII) with an organometallic compound PhM in which Ph represents a phenyl group and M represents Li, MgX or ZnX with X being a halide selected from I, Br and Cl to obtain the compound of formula (V)

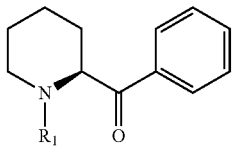

(V)

(iii) reduction of the compound of formula (V) by an alkaline salt of tri-sec-butylborohydride to obtain the alcohol of formula (VI) or a salt thereof, in the form of (S,S) enantiomer

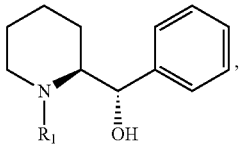

(VI)

(iv) acetylation of the alcohol of formula (VI), optionally followed by deprotection of the amine function of the piperidine group when $R_1$ represents a protecting group, to obtain the (S,S) enantiomer of alpha-phenyl(piperidin-2-yl)methanol acetate.

The particular embodiments described for preparing the compound of formula (VI) in the form of (S,S) enantiomer are transferable to the method of preparing the dextrophacetoperane according to the invention.

It goes without saying that each step of the method according to the invention can be carried out in the presence of a solvent and, optionally, in the presence of a base or an acid.

Formulation

The present invention provides a pharmaceutical composition comprising a compound described above, alone or mixed, and a pharmaceutically acceptable vehicle.

The compositions according to the invention can be administered in various ways and in various forms. Thus, they can be administered systemically, by the oral route, by inhalation or by injection, for example by the intravenous, intramuscular, subcutaneous, transdermal, intraarterial route, etc., the intravenous, intramuscular, subcutaneous, and oral routes and by inhalation being preferred. For injections, the compounds are generally packaged in the form of liquid suspensions, which can be injected by means of syringes or by infusion, for example. In this respect, the compounds are generally dissolved in saline, physiological, isotonic, buffered, solutions etc., compatible with pharmaceutical use and known by a person skilled in the art. Thus, the compositions can contain one or more agents or vehicles selected from dispersants, solubilizers, stabilizers, preservatives, etc. Agents or vehicles usable in liquid and/or injectable formulations are notably methylcellulose, hydroxymethylcellulose, carboxymethylcellulose, polysorbate 80, mannitol, gelatin, lactose, vegetable oils, acacia, etc.

The compounds can also be administered in the form of gels, oils, tablets, suppositories, powders, hard capsules, soft capsules, aerosols, etc., optionally by means of pharmaceutical forms or devices ensuring prolonged and/or delayed release. For this type of formulation, an agent such as cellulose, carbonates or starches is used advantageously.

In a preferred embodiment, the compound is used in a form suitable for administration by the oral route.

Preferably it can be in a form suitable for prolonged release.

More preferably, it can moreover be in the form of a combination or of a mixture of microgranules for immediate release, and of microgranules for prolonged release.

Therapeutic Indications

The invention relates to the treatment of a disorder of attention, more particularly of attention deficit hyperactivity disorder (ADHD), with alpha-phenyl(piperidin-2-yl)methanol, or the pharmaceutically acceptable salts and esters thereof, in particular the acetate derivative, more particularly dextrophacetoperane.

The compound can be administered in monotherapy or in combination with one or more other active principles, including psychostimulants (such as methylphenidate or amphetamine).

In general, the compounds of the invention can be useful for treating, in any subject (adult or child), sleep disorders or disorders of maintaining wakefulness (narcolepsy, hypersomnia), mood disorders, behavioural disorders (agitation, instability), oppositional disorder (with or without provocation), anxiety disorders, personality disorders (pervasive developmental disorder, borderline states, schizophrenia), Alzheimer's disease, old-age dementias (fronto-temporal dementia, cortico-basal dementia, Lewy body disease), Parkinson's disease, Gilles de la Tourette syndrome, essential tremor, and restless legs syndrome (RLS).

Finally, a method is described for treating these disorders or diseases, in particular attention deficit hyperactivity disorder (ADHD), in a patient requiring such a treatment, said method comprising administering, to said patient, a therapeutically effective amount of alpha-phenyl(piperidin-2-yl)methanol, or the pharmaceutically acceptable salts and esters thereof, in particular the acetate derivative, more particularly dextrophacetoperane.

For treating a disorder of attention, and in particular ADHD, daily doses of about 5 to 1000 mg, preferably about 5 to 500 mg, more preferably 5 to 100 mg, more preferably about 5 to 30 mg, 5 to 20 mg, or 5 to 10 mg, are preferred. Divided doses are preferably administered to the patient.

The examples and figures illustrate the invention without limiting its scope.

1. Example of Synthesis of Dextrophacetoperane Hydrochloride:

Dextrophacetoperane hydrochloride was obtained according to the following synthesis scheme in the form of a white powder in a total yield from 20% to 25% and with a purity above 97%.

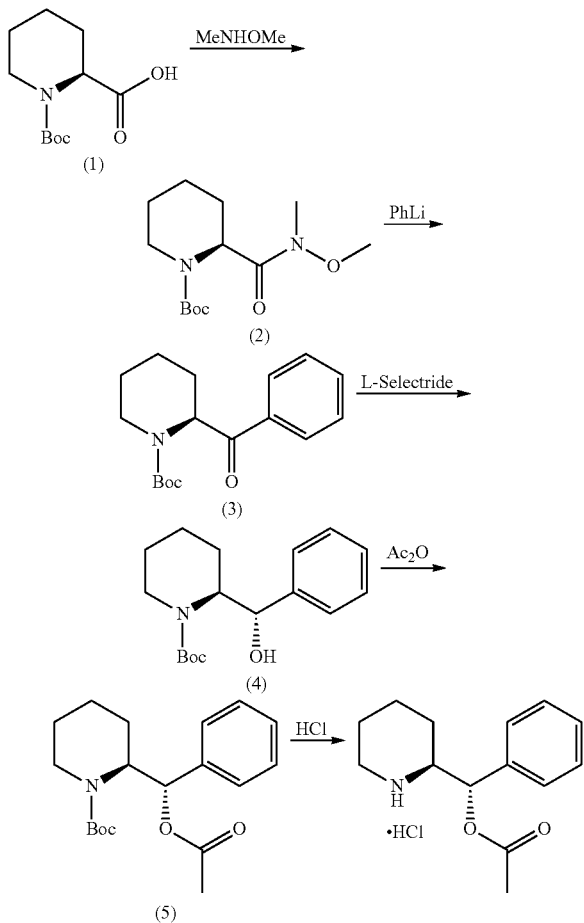

Under a nitrogen atmosphere, the acid (1) (0.5 g, 2.13×10$^{-3}$ mol) is dissolved in $CH_2Cl_2$. N—O-dimethylhydroxylamine hydrochloride (0.254 g, 2.55×10$^{-3}$ mol) and triethylamine (7.51×10$^{-3}$ mol) are added to this solution. Benzotriazol-1-yl-oxy-tris-(dimethylamino)-phosphonium hexafluorophosphate (BOP) (1.06 g, 2.343×10$^{-3}$ mol) is then added, and the reaction mixture is stirred for 6 h. The reaction mixture is then diluted in $CH_2Cl_2$ and transferred to a dropping funnel containing 1M HCl. The organic phase is washed with $NaHCO_3$, then with saturated NaCl, and finally with water. It is dried over $Na_2SO_4$ and then, after filtration and evaporation of the solvent, the oil obtained is purified by flash chromatography (cyclohexane/ethyl acetate 8:2) to give the hydroxamate (2) (0.479 g, 83%).

The hydroxamate (2) (0.470 g, 1.72×10$^{-3}$ mol) is dissolved in ethyl ether, put under a nitrogen atmosphere and cooled to −23° C. Phenyllithium (1.8M in dibutyl ether, 0.955 mL, 1.72×10$^{-3}$ mol) is then added. After stirring for 3 h, the reaction mixture is added to a 1M solution of $KH_2PO_4$ with crushed ice. The aqueous phase is extracted with ethyl acetate, dried, filtered and evaporated. The oil obtained is purified by flash chromatography (cyclohexane/ethyl acetate 8:2) to give the ketone (3) (0.253 g, 52%).

The ketone (3) (0.365 g, 1.26×10$^{-3}$ mol), in anhydrous THF and under a nitrogen atmosphere, is cooled to −78° C.

L-Selectride (1M in THF, 3.79 mL, 3.78×10$^{-3}$ mol) is then added. After stirring for 5 h at this temperature, water and then 35% hydrogen peroxide are added to the reaction mixture, which is then stirred for 2 h. The solution obtained is then diluted in water and ethyl acetate, and the aqueous phase is extracted with ethyl acetate. The combined organic phases are washed with water, then with saturated NaCl, dried over $Na_2SO_4$, then filtered and finally evaporated. The oil obtained is purified by flash chromatography (cyclohexane/ethyl acetate 8:2) to give the alcohol (4) (0.277 g, 76%).

The alcohol (4) (0.2659, 0.91×10$^{-3}$ mol), triethylamine (0.378 mL, 2.73×10$^{-3}$ mol), 4-DMAP (5.55 mg, 4.55×10$^{-5}$ mol) and acetic anhydride (0.516 mL, 5.46×10$^{-3}$ mol) are stirred at room temperature for 14 h. The solution is then basified with 10% $K_2CO_3$ and extracted with ethyl ether. The combined organic phases are dried over $Na_2SO_4$, then filtered and evaporated. The product obtained is purified by flash chromatography (cyclohexane/ethyl acetate 8:2) to give the acetate (5) (0.291 g, 95%).

The acetate (5) (5.7 mg, 1.71×10$^{-5}$ mol) is dissolved in ethyl ether, and 12N hydrochloric acid (0.02 mL) is then added. After stirring for 15 minutes, the solution is evaporated and dried using a vane pump to give dextrophacetoperane (4 mg, 87%) in the form of a white powder.

The product obtained has the following characteristics:

$^1$H NMR (300 MHz, MeOD), δ in ppm: 7.46 (m, 5H), 5.73 (d, J=9 Hz, 1H), 3.69 (m, 1H), 3.50 (d, J=12 Hz, 1H), 3.36 (water in deuterated methanol), 3.11 (t, J=9 Hz, 1H), 2.18 (s, 3H), 1.52-1.97 (m, 6H)

$^{13}$C NMR (75 MHz, MeOD), δ in ppm: 171.2, 136.9, 130.5, 130.1 (2C), 128.6 (2C), 77.5, 60.5, 46.3, 26.5, 23.2, 22.5, 20.9.

IR (cm$^{-1}$): 1741, 1223, 1023, 769, 703

Rotatory power: $[\alpha]^{589}{}_D$=+40 (c=0.05 MeOH)

Enantiomeric excess >90%

TLC: Rf=0.43 with DCM/MeOH eluent

Mass spectrometry (ESI): 234 ([M+1]+

2. Example of Biological Test: Behavioural Study of the Rat Submitted to the T-Maze Test, a Model of ADHD 2.1. Model:

The T-maze behavioural test makes it possible to measure the ability to wait that is displayed by a juvenile animal (here, the rat) when it is given a choice between a quick and immediate food reward or a large but deferred reward. This test allows assessment of the ability to wait, i.e. the level of impulsiveness. In young Wistar rats, methylphenidate (Ritalin®) seems to increase the number of times the large but deferred reward is chosen. This result is also what is found with other amphetamine-type stimulants (amphetamine), with the "non-stimulant" noradrenaline reuptake inhibitors (atomoxetine, mazindol), but also with the eugregoric agents (modafinil, lauflumide).

Since these drugs reduce the symptoms (such as impulsiveness of ADHD), the T-maze test, in juvenile animals, is appropriate for testing for improvement in control of impulsiveness by drugs for treating ADHD.

2.2. Objective:

To show whether phacetoperane, administered intraperitoneally (IP) at equivalent dose of that of methylphenidate, improves the ability to wait in young Wistar rats submitted to the T-maze test. An improvement in the ability to wait by this compound would indicate that this compound reduces impulsiveness and consequently could be useful in the treatment of ADHD. Methylphenidate is used as reference product in this experiment.

2.3. Protocol:

The experiments were carried out between 8 h and 18 h at room temperature (22±1.5° C.) under artificial lighting in calm conditions.

Male AF Wistar rats were used (Centre d'Elevage René Janvier, France), aged 22 days at the start of the experiment and between 30 and 42 days at the time of administration of the molecules.

The molecules tested are:
methylphenidate (MPH): 3 mg/kg intraperitoneally (IP)
phacetoperane (compound in racemic form designated BLK-010 in this test): 1 mg/kg intraperitoneally (IP)
placebo: 1 mL/kg intraperitoneally (IP)

The experiments were carried out in two identical T-maze devices made of opaque grey plastic tubing (inside diameter 7.5 cm), consisting of a start area (30 cm long), a transparent plastic box (width 10 cm, depth 10 cm, height 10 cm) and two arms (35 cm long) each leading to a rectangular box made of black plastic (width 18 cm, depth 30 cm, height 10 cm). Cf. FIG. 1. Detachable guillotine doors of grey plastic can be inserted in vertical slits, located at the entrance to the start area and at each end of the arms. One of the goal boxes (left or right, depending on the rats) is constantly supplied with a large reward, the other one with a small reward. Large and small rewards consist, respectively, of 5 pellets and 1 pellet (20 mg, Technical & Scientific Equipment GmbH, Germany). The pellets are placed in a translucent dish before each test.

Training Phases

1st Phase—Accustoming.

The animals are first submitted to two to six sessions of 5 min of accustoming. The rat is gently placed in the start area, which is then closed with a guillotine door inserted in the slit. The animal is allowed to explore the device freely and eat rewards placed in dishes.

2nd Phase—Pre-Training.

After a door has been placed in slit c2 near each goal box, the rat is placed in the start area. When it enters one of the two arms, a door is inserted behind it in slit c1 near the choice area and the door placed in slit c2 is removed. Once the animal enters the goal box, the door is replaced in slit c2. The rat is recovered from the goal box once it has eaten the pellets. The animal is then put back in its cage for 2 to 3 min. Each rat is submitted one to three times per day to five test sessions. In 4 to 12 sessions, the rat selects the arm giving access to the large reward in more than 80% of the tests. Training then begins.

3rd Phase: Training.

The rats follow 1 to 4 times/day training sessions of 5 tests during which a delay is introduced before access to the large reward. After a door has been placed in slit c2 near each goal box, the rat is placed in the start area. When it enters one of the two arms, a second door is inserted behind it in slit c1 near the choice area, so that the rat choosing the arm leading to the large reward can be detained in this arm for 30 s—the waiting delay—before gaining access to the reinforcement. Otherwise, if the animal chooses the arm leading to the small reward, the door placed in slit c2 is opened immediately, allowing the animal to enter the goal box. Drug testing begins when the animal chooses the large reward delayed by 30 s in 2 tests out of 5 (or less) during two consecutive sessions and in 1 test out of 5 (or less) in the next session. The animals that do not meet this criterion for 12 sessions are eliminated from the experiment.

The testing phases take place as follows:
2 sessions of "pre-medication" control ("cont-pre"),
2 "medication" sessions,
2 sessions of "post-medication" control ("cont-post").

Two sessions of pre-medication control are carried out on the same day, with an interval of 2 to 4 h. Medication sessions 1 and 2 are carried out for one and two days, respectively, after the sessions of pre-medication control. The two sessions of post-medication control are carried out for one day after medication session 2. BLK-10, methylphenidate or placebo are administered before each medication session.

The animals are distributed at random into 3 groups (n=6 animals/group) and receive a total of two intraperitoneal administrations (one before each medication session) of
group methylphenidate (3 mg/kg) 30 min before the test,
group BLK-010 (1 mg/kg) 30 min before the test 2.4 Results Analysis of the data was carried out for each animal and the percentage of choices of "large but deferred reward" was calculated as well.

The results are given in Table 1.

TABLE 1

| | | Cont-Pre | Medication | Cont-Post |
|---|---|---|---|---|
| Placebo IP—60 min | Mean | 1.17 | 1.17 | 1.50 |
| (n = 6) | Standard deviation | 0.31 | 0.40 | 0.34 |
| | ≠ vs. Cont-Pre: p = | | 1.000 | 0.465 |
| | ≠ vs. Cont-Post: p = | 0.465 | 0.465 | |
| Methylphenidate | Mean | 1.17 | 3.67 | 0.83 |
| 3 mg/kg IP—30 min | Standard deviation | 0.31 | 0.33 | 0.17 |
| (n = 6) | ≠ vs. Cont-Pre: p = | | 0.007 | 0.363 |
| | ≠ vs. Cont-Post: p = | 0.363 | 0.001 | |
| Phacetoperane | Mean | 1.17 | 4.17 | 0.33 |
| (BLK-010) | Standard deviation | 0.31 | 0.65 | 0.21 |
| 1 mg/kg IP—30 min | ≠ vs. Cont-Pre: p = | | 0.003 | 0.042 |
| (n = 6) | ≠ vs. Cent-Post: p = | 0.042 | 0.001 | |

Methylphenidate, used as reference product, and BLK-010 are administered before the test. These two molecules improve the ability to wait in young Wistar rats submitted to the T-maze test relative to the control.

The compound BLK-010 appears significantly and statistically more effective than methylphenidate in the ability to wait in young Wistar rats submitted to the T-maze test.

The compound BLK-010 is the only molecule that gives significant improvement in the behaviour of the juvenile rat between "pre-treatment" and "post-treatment" and appears significantly and statistically more effective than methylphenidate in the ability to wait in young Wistar rats submitted to the T-maze test (p=0.042). Improvement of impulsiveness is found in all the animals (n=6) treated with the compound BLK-010 (phacetoperane) (1 mg/kg). The latter is significantly better than that found with methylphenidate (3 mg/kg) (cf. FIG. 2).

Phacetoperane (1 mg/kg) does not lead to any habituation, nor even expenditure (before and after treatment). It is robust over time (during the different tests) and is always found to be more effective than methylphenidate (3 mg/kg).

The invention claimed is:

1. A method for treating an attention deficit hyperactivity disorder (ADHD) in a human patient by at least reducing impulsivity, comprising orally administering to said patient levophacetoperane, or a pharmaceutically acceptable salt thereof, as the sole active ingredient in an amount effective to reduce impulsivity in said patient ranging from about 5 mg to about 20 mg per day.

2. The method of claim 1, wherein the administered amount of levophacetoperane, or a pharmaceutically acceptable salt thereof, ranges from about 5 mg to about 10 mg.

3. The method of claim 2, wherein the human is a child or an adolescent.

4. The method of claim 1, wherein the administered amount of levophacetoperane, or a pharmaceutically acceptable salt thereof, ranges from about 10 mg to about 20 mg.

5. The method of claim 4, wherein the human is an adolescent or an adult.

6. The method of any of claims 1 and 2-5, wherein the levophacetoperane, or a pharmaceutically acceptable salt thereof, is administered as a tablet.

7. The method of claim 1, wherein the administered amount of levophacetoperane, or a pharmaceutically acceptable salt thereof, ranges from about 5 mg to about 15 mg.

8. The method of claim 7, wherein the human is a child or an adolescent.

9. The method of any of claims 7-8, wherein the administered levophacetoperane, or a pharmaceutically acceptable salt thereof, is as a tablet.

\* \* \* \* \*